US 8,855,396 B2

(12) United States Patent
Kargar et al.

(10) Patent No.: US 8,855,396 B2
(45) Date of Patent: Oct. 7, 2014

(54) SYSTEM FOR DETECTING AN INVASIVE ANATOMICAL INSTRUMENT

(75) Inventors: Soroosh Kargar, Lake in the Hills, IL (US); Weng Lei, Mount Prospect, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 594 days.

(21) Appl. No.: 13/015,656

(22) Filed: Jan. 28, 2011

(65) Prior Publication Data

US 2011/0293163 A1 Dec. 1, 2011

Related U.S. Application Data

(60) Provisional application No. 61/347,853, filed on May 25, 2010.

(51) Int. Cl.
*G06K 9/00* (2006.01)
*G06K 9/32* (2006.01)
*G06T 7/00* (2006.01)

(52) U.S. Cl.
CPC ........ *G06K 9/3233* (2013.01); *G06K 2209/057* (2013.01); *G06T 2207/30021* (2013.01); *G06T 2207/10116* (2013.01); *G06T 7/0044* (2013.01)
USPC ........................................................ 382/132

(58) Field of Classification Search
CPC .................. G06T 2207/30101; G06T 7/0012; G06T 2207/10121
USPC ............................ 382/132, 128, 131; 600/424
See application file for complete search history.

(56) References Cited

U.S. PATENT DOCUMENTS

| | | | | |
|---|---|---|---|---|
| 4,868,651 A * | 9/1989 | Chou et al. | .................... | 378/98.7 |
| 6,055,340 A * | 4/2000 | Nagao | ............................ | 382/261 |
| 6,233,476 B1 * | 5/2001 | Strommer et al. | ............. | 600/424 |
| 6,493,575 B1 * | 12/2002 | Kesten et al. | .................. | 600/431 |
| 7,397,953 B2 * | 7/2008 | Said | .............................. | 382/199 |
| 7,801,343 B2 * | 9/2010 | Unal et al. | ..................... | 382/128 |
| 7,835,785 B2 | 11/2010 | Scully | | |
| 8,208,989 B2 * | 6/2012 | Maschke et al. | .............. | 600/424 |
| 8,295,911 B2 * | 10/2012 | Heigl | ............................. | 600/424 |
| 2004/0015778 A1 * | 1/2004 | Britton et al. | ................. | 715/500 |
| 2005/0143651 A1 | 6/2005 | Verard et al. | | |
| 2005/0182319 A1 * | 8/2005 | Glossop | ........................ | 600/424 |
| 2005/0203371 A1 * | 9/2005 | Kleen | ........................... | 600/424 |
| 2007/0016108 A1 * | 1/2007 | Camus et al. | ................. | 600/587 |
| 2008/0027889 A1 * | 1/2008 | Zhou et al. | ...................... | 706/50 |
| 2009/0226063 A1 | 9/2009 | Rangwala et al. | | |
| 2010/0022873 A1 | 1/2010 | Hunter et al. | | |

(Continued)

*Primary Examiner* — Matthew Bella
*Assistant Examiner* — Dennis Rosario
(74) *Attorney, Agent, or Firm* — Brennan K Bradley

(57) ABSTRACT

A system identifies a stent in an image using luminance density and anatomical information. An X-ray imaging system automatically detects and indicates location of an invasive anatomical device in an image. An interface acquires, data representing X-ray images of patient vessels and data identifying a particular vessel containing a medical device. An image data processor employs a model of anatomical vessels to select a region of interest in a vessel identified by the acquired data and automatically determines a location of the medical device in an acquired image by determining at least a portion of an outline of the medical device by detecting a luminance transition in the acquired image using an image edge detector. A display processor initiates generation of data depicting location of the medical device in the acquired image in response to determining the at least a portion of the outline of the medical device.

20 Claims, 11 Drawing Sheets

(56) References Cited

U.S. PATENT DOCUMENTS

| | | | |
|---|---|---|---|
| 2010/0066770 A1* | 3/2010 | Fredlund et al. | 345/691 |
| 2010/0157041 A1* | 6/2010 | Klaiman et al. | 348/77 |
| 2010/0240986 A1 | 9/2010 | Stiles | |
| 2010/0283484 A1 | 11/2010 | Cohen et al. | |
| 2010/0284591 A1 | 11/2010 | Arnon et al. | |
| 2010/0312096 A1 | 12/2010 | Guttman et al. | |

* cited by examiner

| Anatomic Region of Heart | Coronary Artery (most likely associated) |
|---|---|
| Inferior | Right coronary |
| Anteroseptal | Left anterior descending |
| Anteroapical | Left anterior descending (distal) |
| Anterolateral | Circumflex |
| Posterior | Right coronary artery |

SYSTEM FOR DETECTING AN INVASIVE ANATOMICAL INSTRUMENT

This is a non-provisional application of provisional application Ser. No. 61/347,853 filed May 25, 2010, by S. Kargar et al.

FIELD OF THE INVENTION

This invention concerns an X-ray imaging system for detecting and displaying an invasive anatomical device by using a model of anatomical vessels to select a region of interest in a vessel and automatically determining a location of the medical device in an acquired image based on image data processing.

BACKGROUND OF THE INVENTION

It is difficult for a physician to identify a stent by visual review of an X-ray image. A stent may become obscured by tissue growing on, and within, a deployed stent (invasive anatomical device) in a coronary vessel, for example. A system according to invention principles automatically processes Image data (e.g. X-ray or other image data) to identify a stent that was previously deployed in a coronary vessel of a patient.

SUMMARY OF THE INVENTION

A system identifies a stent in an image using luminance density and anatomical information for a coronary heart disease follow up visit, for example. An X-ray imaging system automatically detects and indicates location of an invasive anatomical device in an image. An interface acquires, data representing X-ray images of patient vessels and data identifying a particular vessel containing a medical device. An image data processor employs a model of anatomical vessels to select a region of interest in a vessel identified by the acquired data and automatically determines a location of the medical device in an acquired image by determining at least a portion of an outline of the medical device by detecting a luminance transition in the acquired image using an image edge detector. A display processor initiates generation of data depicting location of the medical device in the acquired image in response to determining the at least a portion of the outline of the medical device.

BRIEF DESCRIPTION OF THE DRAWING

FIG. 1 shows a table indicating regions of the heart that are supplied by different coronary arteries.

DETAILED DESCRIPTION OF THE INVENTION

Figure 4:
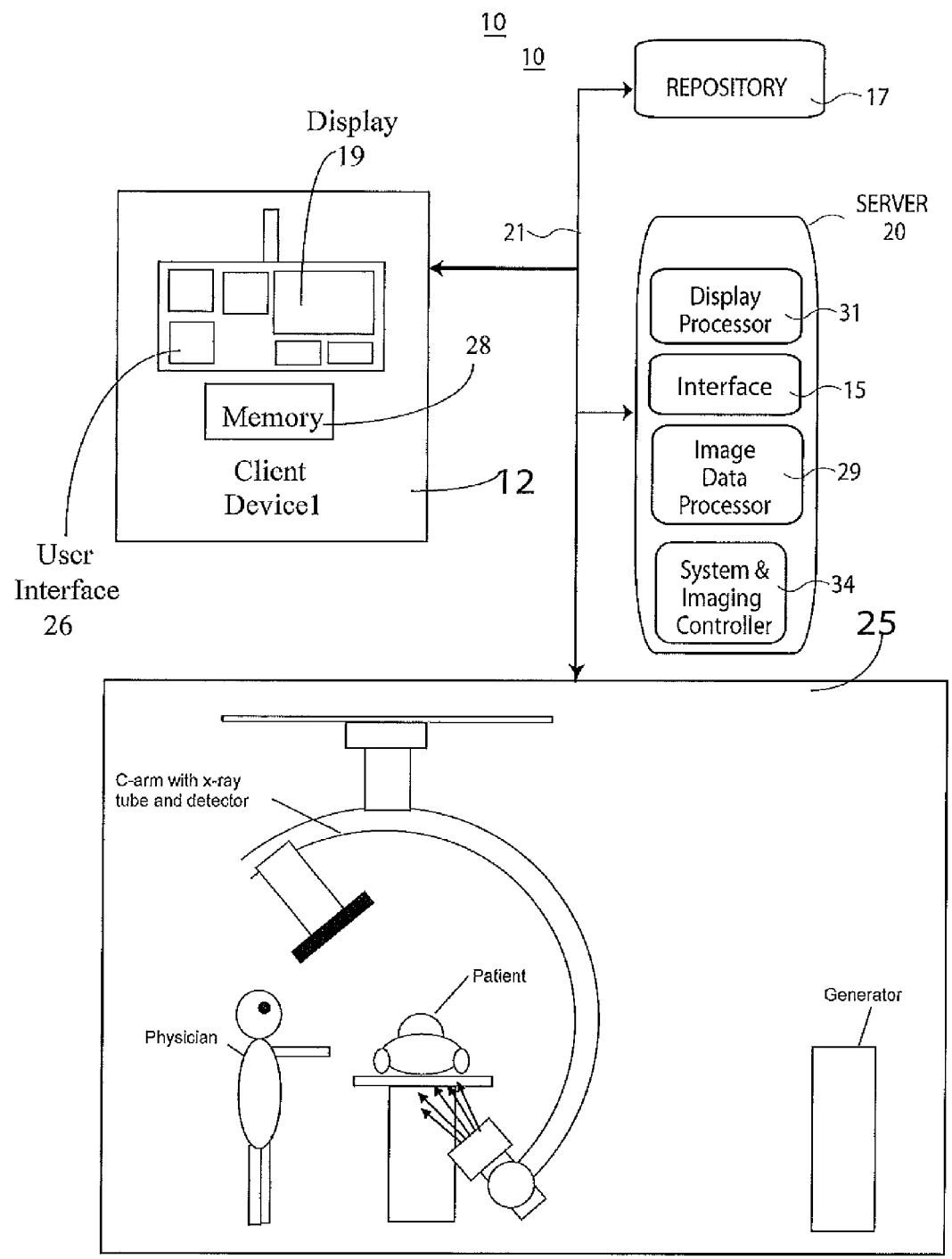
FIG. 4 shows an X-ray imaging system that automatically detects and displays an invasive anatomical device in an image, according to invention principles.

A system according to invention principles automatically processes image data using luminance intensity (luminance density) and anatomical information to identify a stent in an image for a coronary heart disease follow up visit, for example. The system advantageously locates a stent that was previously installed to provide stent presentation information for use during a post-stent insertion patient follow up visit, for example. FIG. 4 shows X-ray imaging system 10 that automatically detects and displays an invasive anatomical device in an image. System 10 includes one or more processing devices (e.g., workstations or portable devices such as notebooks, Personal Digital Assistants, phones) 12 that individually include a user interface control device 26 such as a keyboard, mouse, touchscreen, voice data entry and interpretation device, display 19 and memory 28. System 10 also includes at least one repository 17, X-ray imaging modality system 25 (which in an alternative embodiment may comprise an MR (magnetic resonance), CT scan, or Ultra-sound system, for example) and server 20 intercommunicating via network 21. X-ray modality system 25 comprises a C-arm X-ray radiation source and detector device rotating about a patient table and an associated electrical generator for providing electrical power for the X-ray radiation system. The display images are generated in response to predetermined user (e.g., physician) specific preferences.

At least one repository 17 stores medical image studies for multiple patients in DICOM compatible (or other) data format. A medical image study individually includes multiple image series of a patient anatomical portion which in turn individually include multiple images. Server 20 includes interface 15, display processor 31, image data processor 29 and system and imaging controller 34. Display 19 presents display images comprising a Graphical User Interface (GUI). Imaging controller 34 controls operation of imaging device 25 in response to user commands entered via user interface 26. In alternative arrangements, one or more of the units in server 20 may be located in device 12 or in another device connected to network 21.

Interface 15 acquires, data representing X-ray images of patient vessels and data identifying a particular vessel containing a medical device. Image data processor 29 employs a model of anatomical vessels to select a region of interest in a vessel identified by the acquired data. Further, processor 29 automatically determines a location of the medical device in an acquired image (an X-ray 2D image) by determining at least a portion of an outline of the medical device by detecting a luminance transition in the acquired image using an image edge detector. Display processor 31 initiates generation of data depicting location of the medical device in the acquired image in response to determining the at least a portion of the outline of the medical device.

Figure 2:
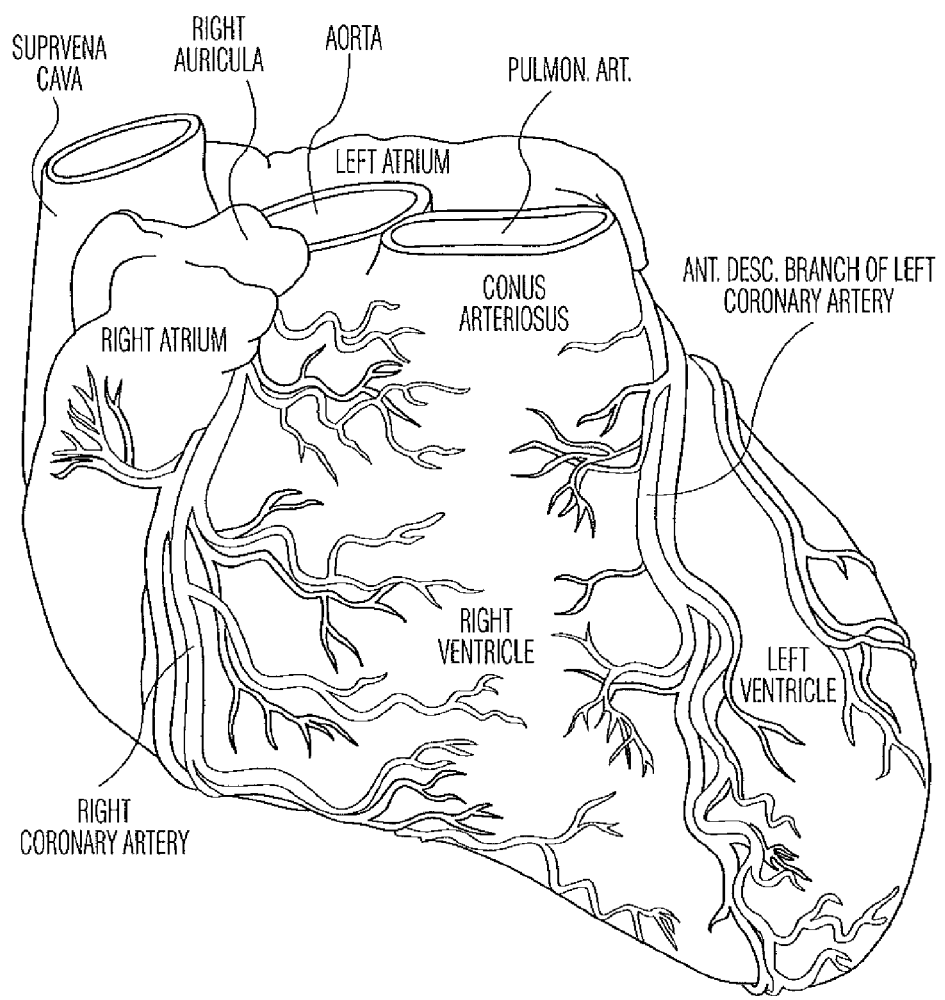
FIG. 2 shows an anterior view of the heart indicating a right coronary artery and anterior descending branch of the left coronary artery.
Figure 3:
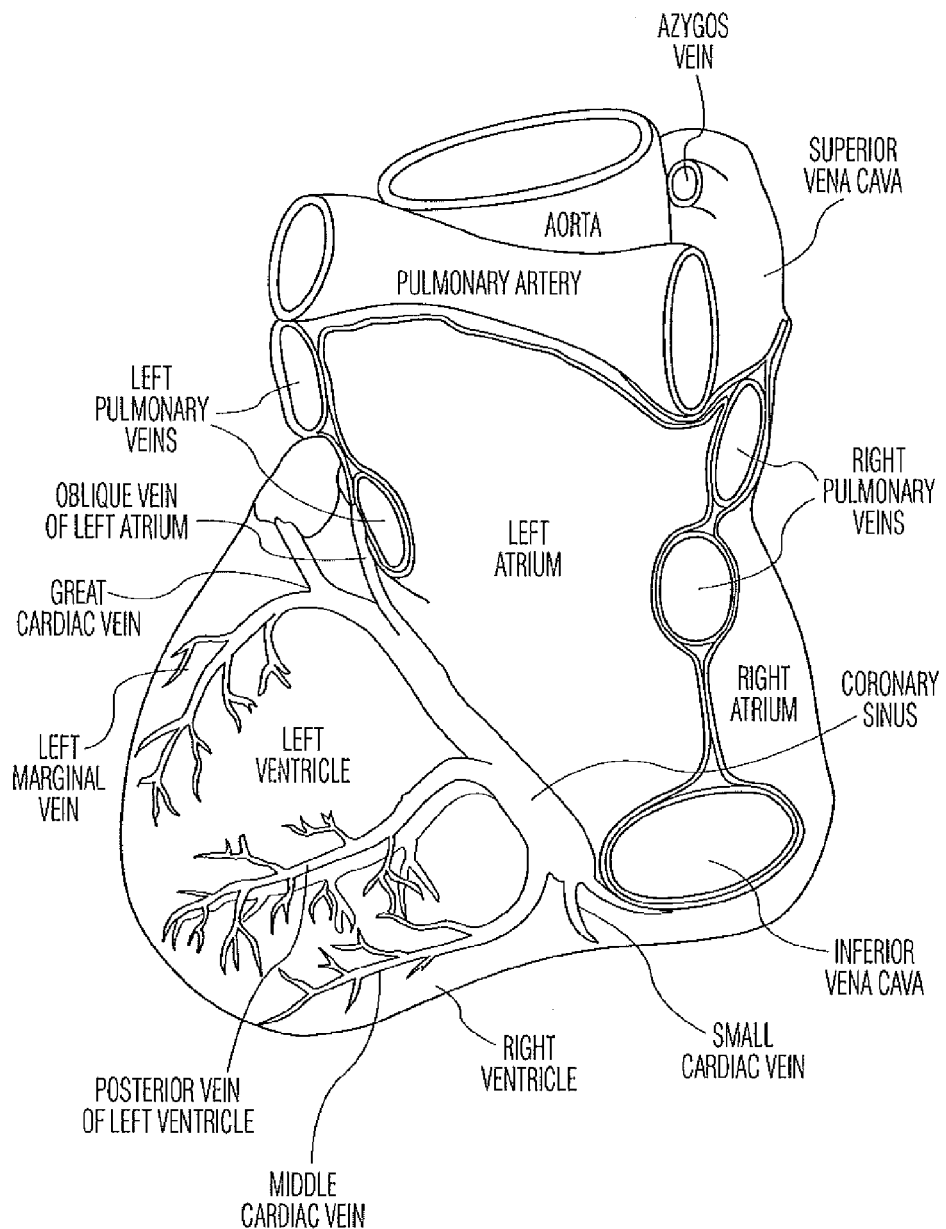
FIG. 3 shows base and diaphragmatic surface of heart.
Figure 5:
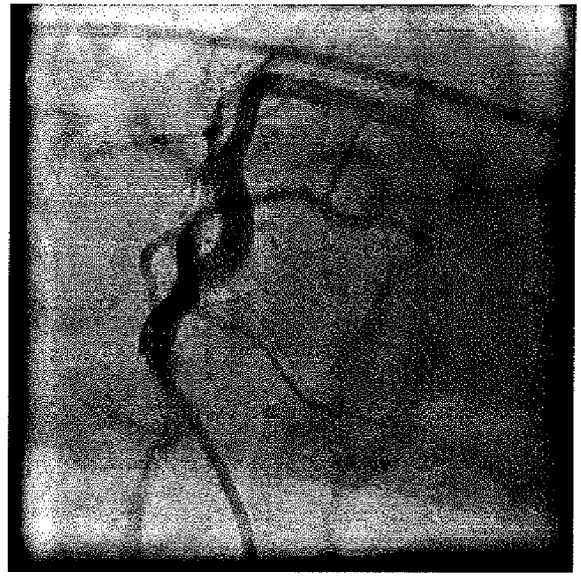
FIG. 5 shows an input image specifically, a Left Coronary Artery (LCA) image.
Figure 10:
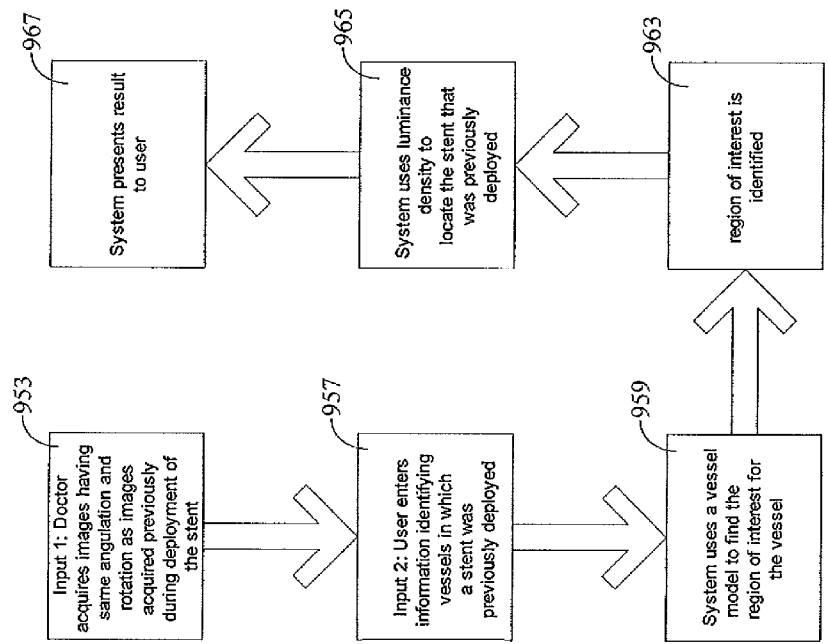
FIG. 10 shows a flowchart of a process and workflow used for locating an invasive anatomical device in an image, according to invention principles.

FIG. 10 shows a flowchart of a process and workflow used for locating an invasive anatomical device (e.g., a stent) in an image and displaying an image identifying the boundary of the device. In step 953, a physician uses an imaging modality device (X-ray imaging system 25 FIG. 4) to acquire images having the same angulation and degree of rotation as images that were previously acquired using system 25 during deployment of a stent. X-ray imaging system 25 employs a predetermined set of angulation (angles) for acquisition of left and right coronary vessel angiograms. FIG. 1 shows a table indicating different regions of the heart that are supplied by different coronary arteries. For example, viewing of a right coronary vessel is around LAO (left anterior oblique) 21, CAUD (caudal) 7 and viewing of a left coronary vessel is around RAO (right anterior oblique) 24, CRAN (cranial) 41. FIG. 2 shows an anterior view of the heart indicating a right coronary artery and anterior descending branch of the left coronary artery. FIG. 3 shows base and diaphragmatic surfaces of a heart. FIG. 5 shows an input image specifically, a Left Coronary Artery (LCA) image acquired at the same orientation, angulation and degree of rotation as images that were previously acquired using system 25 during deployment of a stent.

In step 957, system 10 prompts a user via a display image presented on display 19 to enter information identifying a vessel within which a stent was previously deployed (e.g., a left coronary artery, or right coronary artery). This information is presented as a selection option (e.g. by presenting pictures of the different vessels and by prompting a user to graphically select a particular vessel or vessels) or as a text field. The vessel location information may also be acquired by automatically interrogating other sources such as a patient electronic medical record for the information.

Figure 6:
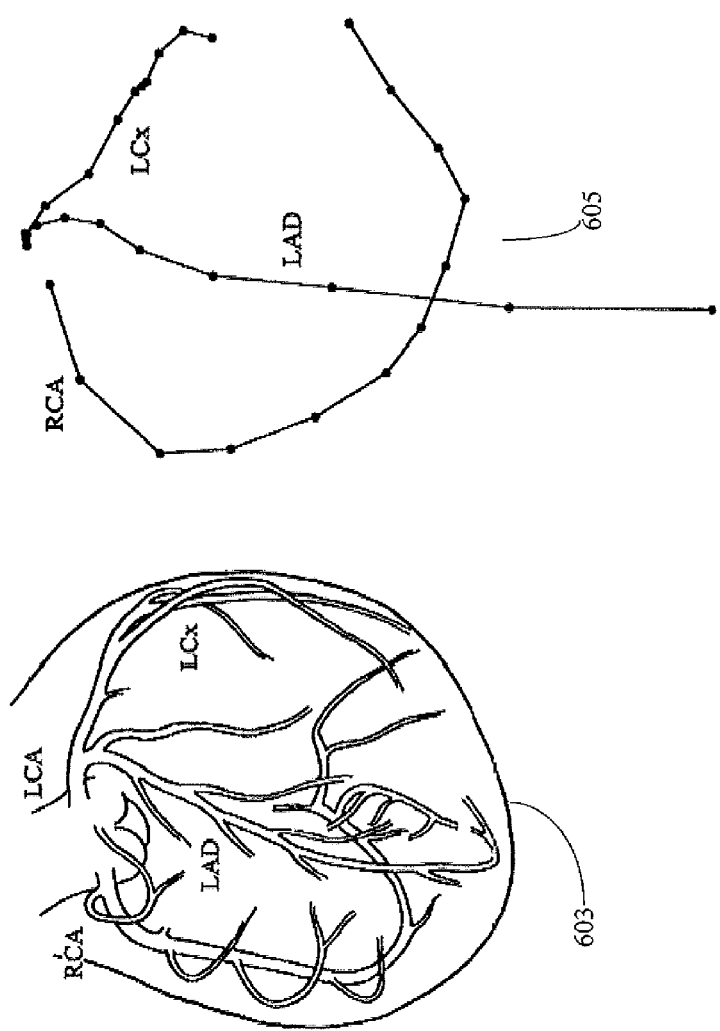
FIG. 6 shows a vessel model, according to invention principles.

In response to acquisition of vessel identification information e.g., of a coronary vessel containing a deployed stent, system 10 in step 959 employs a vessel model to find a region of interest of the vessel. FIG. 6 shows a diagram of the heart 603 showing principle heart vessels including right coronary artery (RCA), left coronary artery (LCA), left anterior descending (LAD) and left circumflex artery (LCx). System 10 employs a vessel model representation of the heart comprising segmented linearized representations of the vessels as shown in model 605. Specifically, vessel model 605 comprises segmented linearized representations of the RCA, LAD and LCx vessels and corresponding three dimensional (3D) coordinates indicating locations of the individual vessel segments in a 3D volume. Model 605 enables location of the vessels in the 3D volume and visual presentation of the vessels in a 3D image representation of the volume.

In step 963, image data processor 29 automatically determines a region of interest in the identified vessel within which a stent was previously deployed. Image data processor 29 automatically selects a region of interest in the identified vessel by determining a region of interest in the identified vessel from data in a medical record of the patient. Processor 29 determines the region of interest in the identified vessel in response to a text description identifying a location of a device in the identified vessel in the patient medical record. In another embodiment, image data processor 29 automatically overlays and aligns a medical image indicating a medical device with an X-ray image of the patient vessels and selects a region of interest in the identified vessel in response to the medical device location in the overlay image.

Figure 7:
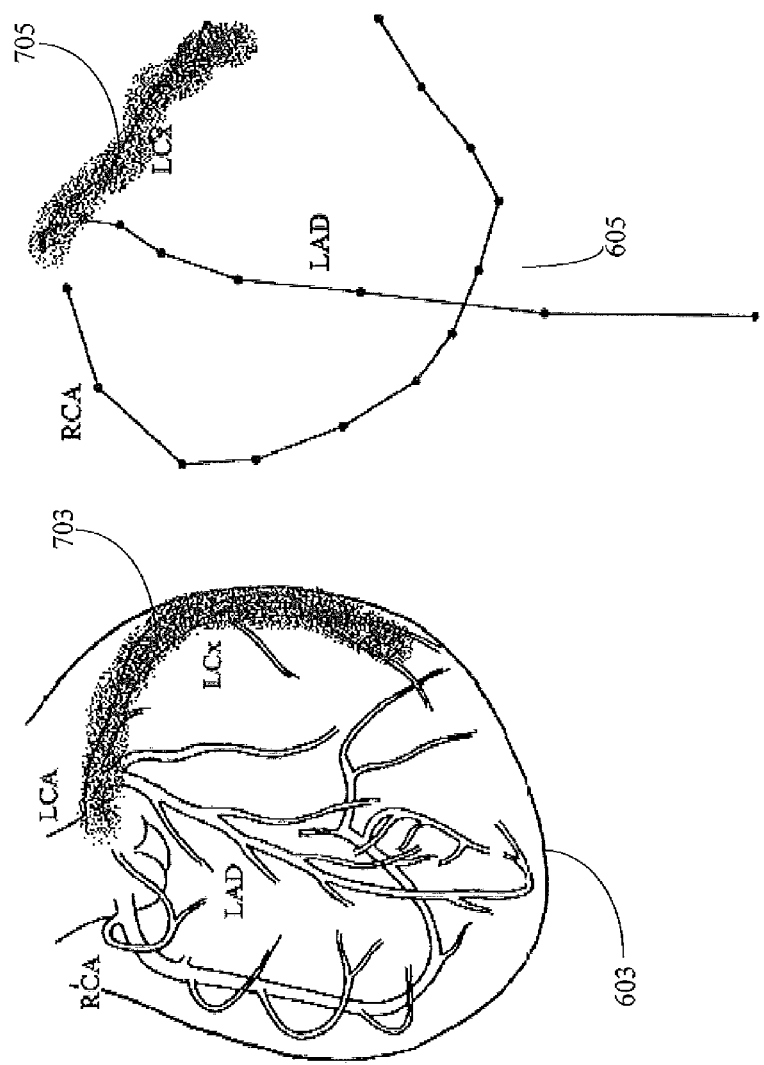
FIG. 7 shows a region of interest identified in the vessel model of FIG. 6, according to invention principles.
Figure 8:
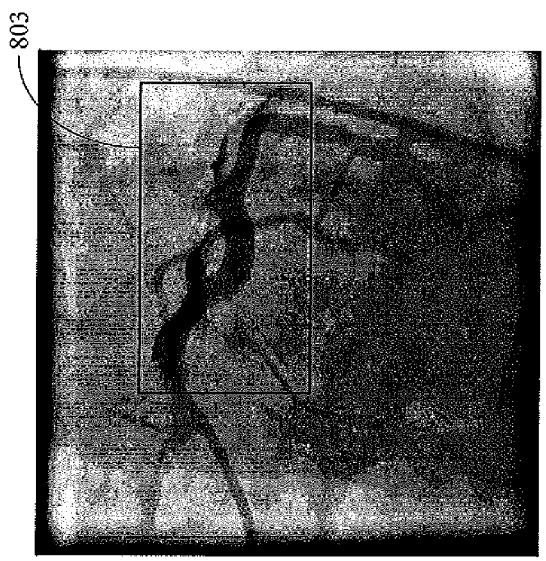
FIG. 8 shows a processed input image indicating an identified region of interest, according to invention principles.

FIG. 7 shows a region of interest identified in the vessel model of FIG. 6 by image data processor 29. Specifically, processor 29 identifies region of interest 705 comprising a left circumflex artery (LCx) in the vessel model representation of the heart comprising segmented linearized representations of the vessels as shown in model 605. Region of interest 705 corresponds to region 703 comprising the left circumflex artery (LCx) in the diagram of the heart 603 showing principle heart vessels. Display processor 31 initiates generation of data depicting location of the determined region of interest in the identified vessel in the acquired image. FIG. 8 shows the processed acquired image indicating identified region of interest 803 in the identified vessel.

In step 965, in response to identification of region of interest 803, image data processor 29 uses luminance density information to locate the stent that was previously deployed within region of interest 803. Image data processor 29 automatically determines a location of the stent in the acquired image by determining at least a portion of an outline of the stent by detecting image luminance density variation information. Processor 29 automatically determines the location of the stent in the acquired image by determining at least a portion of the stent outline by deriving a histogram indicating numbers of pixels in the acquired image having particular luminance intensity values or ranges of values. In step 967 display processor 31 initiates generation of data depicting location of the stent in the acquired image in response to determining the at least a portion of the outline of the medical device.

Figure 9:
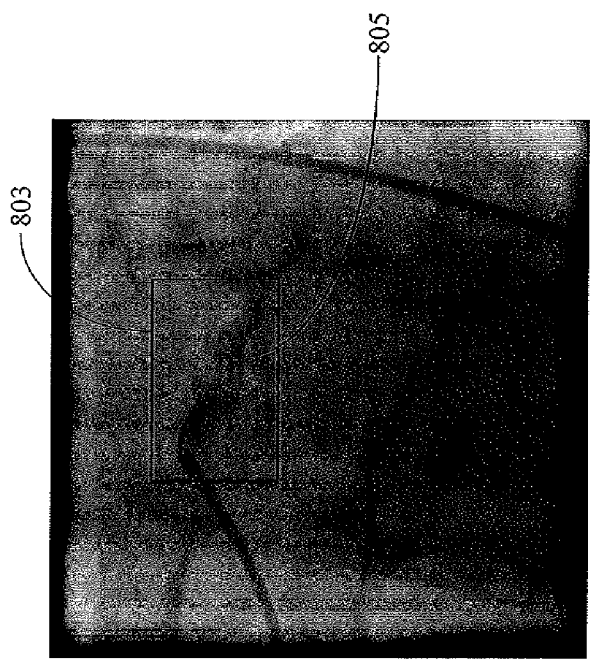
FIG. 9 shows a processed input image indicating an identified region of interest and invasive anatomical device, according to invention principles.

FIG. 9 shows a processed input image indicating an identified region of interest 803 and determined location 805 of the stent in the acquired image. In response to finding the stent, the system provides a display image visually and graphically presenting the stent 805 in anatomical context and position within region of interest 803 to a user. In another embodiment, image data processor 29 indicates where the stent is in the acquired image and region of interest 803 using a text string presented in a displayed image provided by processor 31 for presentation on display 19. Alternatively, image data processor 29 and display processor 31 generates an overlay indicating the stent for superimposition on the acquired image.

Figure 11:
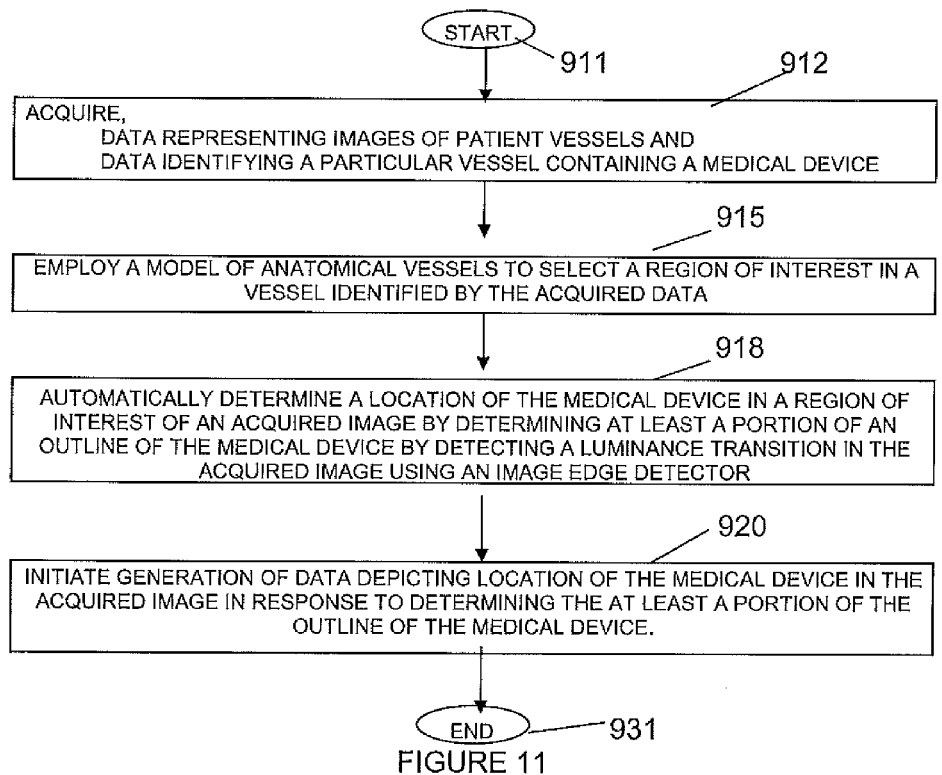
FIG. 11 shows a flowchart of a process used by an X-ray imaging system that automatically detects and displays an invasive anatomical device in an image, according to invention principles.

FIG. 11 shows a flowchart of a process used by imaging system 10 that automatically detects and displays an invasive anatomical device in an image. In step 912 following the start at step 911, interface 15 acquires, data representing images (e.g., X-ray, MR, CT scan Ultrasound images) of patient vessels and data identifying a particular vessel containing a medical device (invasive instrument). The images of patient vessels acquired by interface 15 have the same degree of rotation and orientation as images that were previously acquired during deployment of the medical device. In step 915, image data processor 29 employs a model of anatomical vessels to select a region of interest in a vessel identified by the acquired data. The model of anatomical vessels comprises a data representation of segmented linearized vessels and enables location of a vessel in a 3D volume.

Image data processor 29 selects a region of interest in the vessel by determining a region in the vessel using data acquired from a medical record of the patient. Specifically, in one embodiment processor 29 selects a region of interest in the vessel from a text description identifying a location of a medical device in the vessel acquired from the patient medical record. In another embodiment, image data processor 29 automatically overlays and aligns a medical image indicating a medical device with an image of the patient vessels and selects a region of interest in the vessel in response to the medical device location in the overlay image.

Processor 29 in step 918 automatically determines a location of the medical device in a region of interest of an acquired image by determining at least a portion of an outline of the medical device by detecting a luminance transition in the acquired image using an image edge detector. Image data processor 29 automatically determines a location of the medical device in an acquired image by determining at least a portion of an outline of the medical device by detecting image density (luminance intensity) variation information. In one embodiment processor 29 detects an outline of the medical device by deriving a histogram indicating numbers of pixels in the acquired image having particular luminance intensity values or ranges of values and by comparing a determined number of pixels of one range with the number in another range or with a predetermined threshold number. Display processor 31 in step 920 initiates generation of data depicting location of the medical device in the acquired image in response to determining the at least a portion of the outline of the medical device. Display processor 31 initiates generation of data representing a visual presentation of a vessel in a 3D image representation of the volume. The process of FIG. 11 terminates at step 931.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 4-11 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system uses patient medical information to automatically determine a region of interest of a vessel within an image expected to contain an invasive medical device and processes image data of the region of interest using luminance intensity (density) and edge detection methods to identify luminance transitions indicative of a stent outline in an image for a coronary heart disease follow up visit, for example. Further, the processes and applications may, in alternative embodiments, be located on one or more (e.g., distributed) processing devices on a network linking the units of FIG. 4. Any of the functions and steps provided in FIGS. 4-11 may be implemented in hardware, software or a combination of both.

What is claimed is:

1. An X-ray imaging system for automatically detecting and indicating location of, an invasive anatomical device in an image, comprising:
   an interface for acquiring,
      data representing x-ray images of patient vessels including a particular vessel in which a medical device is located at a position in which the medical device was previously deployed during a previous acquiring of earlier images and
      data identifying said particular vessel containing said previously deployed medical device,
      wherein the previously deployed medical device was deployed in said particular vessel before said acquiring data representing images of patient vessels and said acquiring data identifying said particular vessel containing said previously deployed medical device;
   an image data processor for,
      employing a model of anatomical vessels to select a region of interest in said particular vessel containing said previously deployed medical device identified by the acquired data identifying said particular vessel containing said previously deployed medical device and
      automatically determining a location of said medical device in said selected region of interest in response to said data identifying said particular vessel containing said previously deployed medical device by determining at least a portion of an outline of said medical device by detecting a luminance transition in said acquired image using an image edge detector; and
   a display processor for initiating generation of data depicting location of said medical device in the acquired image in response to determining said at least a portion of said outline of said medical device.

2. A system according to claim 1, wherein
said image data processor selects a region of interest in said vessel by determining a region in said vessel using data acquired from a medical record of said patient.

3. A system according to claim 1, wherein
said image data processor automatically selects a region of interest in said vessel from a text description identifying a location of a device in said vessel acquired from a patient medical record.

4. A system according to claim 1, wherein
said image data processor automatically overlays and aligns a medical image indicating a medical device with an X-ray image of said patient vessels and selects a region of interest in said vessel in response to said medical device location in said overlay image.

5. A system according to claim 1, wherein
said image data processor automatically determines a location of said medical device in an acquired image by determining at least a portion of an outline of said medical device by detecting image density variation information.

6. A system according to claim 1, wherein
said image data processor automatically determines a location of said medical device in an acquired image by determining at least a portion of an outline of said medical device by deriving a histogram indicating numbers of pixels in said acquired image having particular luminance intensity values or ranges of values.

7. A system according to claim 1, wherein
said interface acquires data representing X-ray images of patient vessels having the same degree of rotation and orientation as images that were previously acquired during deployment of said medical device.

8. A system according to claim 1, wherein
said model of anatomical vessels comprises a data representation of segmented linearized vessels including said particular vessel and corresponding three dimensional (3D) coordinates indicating locations of the individual vessel segments in a 3D volume.

9. A system according to claim 1, wherein
said model enables location of a vessel in a 3D volume and
said display processor initiates generation of data representing a visual presentation of a vessel in a 3D image representation of the volume and
said system provides a display image prompting a user to enter information identifying said particular vessel containing said previously deployed medical device.

10. An X-ray imaging system for automatically detecting and indicating location of, an invasive anatomical device in an image, comprising:
an interface for acquiring,
data representing X-ray images of patient vessels including a particular vessel in which a medical device is located at a position in which the medical device was previously deployed during a previous acquiring of earlier images and
data identifying said particular vessel containing said previously deployed medical device,
wherein the previously deployed medical device was deployed in said particular vessel before said acquiring data representing images of patient vessels and said acquiring data identifying said particular vessel containing said previously deployed medical device;
an image data processor for,
selecting a region of interest in a vessel identified by the acquired data by determining a region in said particular vessel containing said previously deployed medical device from data acquired from a medical record of said patient identifying said vessel containing said previously deployed medical device and
automatically determining a location of said medical device in said selected region of interest in response to said data identifying said particular vessel containing said previously deployed medical device by determining at least a portion of an outline of said medical device by detecting a luminance transition in said acquired image using an image edge detector; and
a display processor for initiating generation of data depicting location of said medical device in the acquired image in response to determining said at least portion of said outline of said medical device.

11. A system according to claim 10, wherein
said image data processor automatically selects a region of interest in said vessel from a text description identifying a location of a device in said vessel acquired from said patient medical record.

12. A system according to claim 10, wherein
said image data processor automatically overlays and aligns a medical image indicating a medical device with an X-ray image of said patient vessels.

13. A method used by an imaging system for automatically detecting and indicating location of, an invasive anatomical device in an image, comprising the activities of:
acquiring,
data representing X-ray images of patient vessels including a particular vessel in which a medical device is located at a position in which the medical device was previously deployed during a previous acquiring of earlier images and
data identifying said particular vessel containing said previously deployed medical device,
wherein the previously deployed medical device was deployed in said particular vessel before said acquiring data representing images of patient vessels and said acquiring data identifying said particular vessel containing said previously deployed medical device;
employing a model of anatomical vessels to select a region of interest in said particular vessel containing said previously deployed medical device identified by the acquired data identifying said particular vessel containing said previously deployed medical device and
automatically determining a location of said medical device in said selected region of interest in response to said data identifying said particular vessel containing said previously deployed medical device by determining at least a portion of an outline of said medical device by detecting a luminance transition in said acquired image using an image edge detector; and
initiating generation of data depicting location of said medical device in the acquired image in response to determining said at least a portion of said outline of said medical device.

14. A method according to claim 13, including the activity of
selecting a region of interest in said vessel by determining a region in said vessel using data acquired from a medical record of said patient.

15. A method according to claim 14, including the activity of
automatically selecting a region of interest in said vessel from a text description identifying a location of a device in said vessel using data acquired from a patient medical record.

16. A method according to claim 13, including the activities of
automatically overlaying and aligning a medical image indicating a medical device with an X-ray image of said patient vessels and
selecting a region of interest in said vessel in response to said medical device location in said overlay image.

17. A method according to claim 13, including the activity of
automatically determining a location of said medical device in an acquired image by determining at least a portion of an outline of said medical device by detecting image density variation information and
prompting a user to enter information identifying said particular vessel containing said previously deployed medical device.

18. A method according to claim 13, including the activity of
automatically determining a location of said medical device in an acquired image by determining at least a portion of an outline of said medical device by deriving a histogram indicating numbers of pixels in said acquired image having particular luminance intensity values or ranges of values.

19. A system according to claim 10, wherein
said image data processor selects said region of interest in said particular vessel using a model of anatomical vessels comprising a data representation of segmented linearized vessels including said particular vessel and corresponding three dimensional (3D) coordinates indicating locations of the individual vessel segments in a 3D volume.

20. A method according to claim 13, wherein
said model of anatomical vessels comprises a data representation of segmented linearized vessels including said particular vessel and corresponding three dimensional (3D) coordinates indicating locations of the individual vessel segments in a 3D volume.

* * * * *